US006534635B1

(12) United States Patent
Miyazaki et al.

(10) Patent No.: US 6,534,635 B1
(45) Date of Patent: Mar. 18, 2003

(54) MODIFIED TIMP

(75) Inventors: Kaoru Miyazaki, Kanagawa-ken (JP); Shouichi Higashi, Chiba-ken (JP)

(73) Assignee: Oriental Yeast Co., Ltd., Tokyo (JP)

( * ) Notice: Subject to any disclaimer, the term of this patent is extended or adjusted under 35 U.S.C. 154(b) by 0 days.

(21) Appl. No.: 09/540,530

(22) Filed: Mar. 31, 2000

(30) Foreign Application Priority Data

Apr. 1, 1999 (JP) .......................................... 11-095142

(51) Int. Cl.$^7$ .......................... C07K 1/00; C07K 14/00; C07K 16/00; C07K 17/00; C12N 9/00

(52) U.S. Cl. ........................ 530/402; 530/350; 435/183

(58) Field of Search .............................. 530/402, 350; 435/183

(56) References Cited

U.S. PATENT DOCUMENTS 5,484,735 A * 1/1996 Davis et al.
5,714,465 A * 2/1998 Langely et al.

FOREIGN PATENT DOCUMENTS

| JP | 12570/97 | 1/1997 |
| JP | 104672/97 | 4/1997 |
| JP | 45699/98 | 2/1998 |
| JP | 130237/98 | 5/1998 |
| WO | WO/90/14363 | 11/1990 |

OTHER PUBLICATIONS

Williamson, et al., 1997, Biochemistry, 36:13882–89.*
Butler, J Biol Chem, 1998, 273(2):871–80.*
Gura, "Systems for Identifying New Drugs Are Often Faulty"; Science, 1997, 278:1041–1042.*
Jain, "Barriers to Drug Delivery in Solid Tumors"; Sci. Am., 1994, 271:58–65.*
Curti, "Physical Barriers to Drug Delivery in Tumors"; Crit. Rev. in Oncology/Hematology, 1993, 14:29–39.*
Hartwell et al., "Integrating Genetic Approaches into the Discovery of Anticancer Drugs"; Science, 1997, 278:64–1068.*
Saibou Kougaku, "Degradation of Extracellular Matrixin Cancer: Activation of MMPs Promotes Cancer Cell Invasion and Metastatis", Cell Technology, vol. 17, No. 4, 1998, pp. 523–533.
Docherty et al., "The matrix metalloproteinases and their natural inhibitors: prospects for treating degenerative tissue diseases", Trends in Biotechnology, vol. 10, Jun. 1992, pp. 200–207.
Matrisian, "The Matrix–Degrading Metalloproteinases", BioEssays, vol. 14, No. 7, Jul., 1992, pp. 455–463.
Stetler–Stevenson et al., "Tumor Cell Interactions With The Extracellular Matrix During Invasion And Metastasis", Annu. Rev. Cell Biol., 1993, vol. 9, pp. 541–573.

Liotta, L. A., "Tumor Invasion and Metastases—Role of the Extracellular Matrix: Rhoads Memorial Award Lecture", Cancer Research, vol. 46, Jan. 1986, pp. 1–7.
Collier et al., "H–ras Oncogene–transformed Human Bronchial Epithelial Cells (TBE–1) Secrete a Single Metalloprotease Capable of Degrading Basement Membrane Collagen", The Journal of Biological Chemistry,vol. 263, No. 14, May 15, 1988, pp. 6579–6587.
Wilhelm et al., "SV40–transformed Human Lung Fibroblasts Secrete a 92–kDa Type IV Collagenase Which is Identical to That Secreted by Normal Human Macrophages", The Journal of Biological Chemistry, vol. 264, No. 29, Oct. 15, 1989; pp. 17213–17221.
Overall et al., "Concanavalin A Produces a Matrix–degradative Phenotype in Human Fibroblasts", The Journal of Biological Chemistry, vol. 265, No. 34, Dec. 5, 1990, pp. 21141–21151.
Brown et al., "Independent Expression and Cellular Processing of $M_r$ 72,000 Type IV Collagenase and Interstitial Collagenase in Human Tumorigenic Cell Lines", Cancer Research, 50, Oct. 1, 1990, pp. 6184–6191.
Ward et al., "Tissue inhibitor of metalloproteinases–2 inhibits the activation of 72 kDa progelatinase by fibroblast membranes", Biochimica et Bipphysica Acta, 1079 (1991), pp. 242–246.
Azzam et al., "Collagen–induced Activation of the $M_r$ 72,000 type IV Collagenase in Normal and Milgnant Human Fibroblastoid Cells", Cancer Research, 52, pp. 4540–4544, Aug. 15, 1992.
Sato et al., "A matrix metalloproteinase expresed on the surface of invasive tumour cells", Nature, vol. 370, Jul. 7, 1994, pp. 61–65.
Strongin et al., "Plasma Membrane–dependent Activation of the 72–kDa Type IV Collagenase Is Prevented by Complex Formation with TIMP–2", The Journal of Biological Chemistry, vol. 268, No. 19, Jul. 5, 1993, pp. 14033–14039.
Strongin et al., "Mechanism of Cell Surface Activation of 72–kDa Type IV Collagenase", The Journal of Biological Chemistry, vol. 270, No. 10, Mar. 10, 1995, pp. 5331–5338.
Brooks et al., "Disruption of Angiogenesis of PEX, a Noncatalytic Metalloproteinase Fragment with Integrin Binding Activity", Cell, vol. 92, pp. 391–400, Feb. 6, 1998.
Kinoshita et al., "Processing of a Precursor of 72–Kilodalton Type IV Collagenase/Gelatinase A by a Recombinant Membrane–Type 1 Matrix Metalloproteinase", Cancer Research, 56, Jun. 1, 1996, pp. 2535–2538.

(List continued on next page.)

Primary Examiner—Sheela Huff
Assistant Examiner—Natalie Davis
(74) Attorney, Agent, or Firm—Nixon & Vanderhye P.C.

(57) ABSTRACT

The present invention provides a novel modified TIMP wherein the $NH_2$-terminal α-amino group thereof is modified with an electron-accepting group to substantially lose the ability to bind to a metalloproteinase.

5 Claims, 8 Drawing Sheets

OTHER PUBLICATIONS

Pei et al., "Transmembrane–deletion Mutants of the Membrane–type Matrix Metallooproteinase–1 Process Progelatinase A and Express Intrinsic Matrix–degrading Activity", The Journal of Biological Chemstry, vol. 271, No. 15, Apr. 12, 1996, pp. 9135–9140.

Will et al., "The Soluble Catalytic Domain of Membrane Type 1 Matrix Metallaproteinase Cleaves the Propeptide of Progelatinase A and Initiates Autoproteolytic Activation", The Journal of Biological Chemistry, vol. 271, No. 29, Jul. 19, 1996, pp. 17119–17123.

Lichte et al., "The recombinant catalytic domain of membrane–type matrix metalloproteinase–1 (MT1–MMP) induces activation of progelantinase A and progelantinase A complexed with TIMP–1", FEBS Letters, 397 (1996), pp. 277–282.

Atkinson et al., "Intermolecular Autolytic Cleavage Can Contribute to the Activation of Progelantinase A by Cell Membranes", The Journal of Biological Chemistry, vol. 270, No. 51, Dec. 22, 1995, pp. 30479–30485.

Sato et al., "Cell surface bindng and activation of gelatinase A induced by expression of membrane–type 1–matrix metalloproteinase (MT1–MMP)", FEBS Letters 385 (1996), pp. 238–240.

Gomis–Ruth et al., "Mechanism of inhibition of the human matrix metalloproteinase stromelysin–1 by TIMP–1", Nature, vol., 389, Sep. 4, 1997, pp. 77–81.

Fernandez–Catalan et al., "Crystal structure of the complex formed by the membrane type 1–matrix metalloproteinase with the tissue inhibitor of metalloproteinases–2, the soluble progelatinase A receptor", The EMBO Journal, vol. 17, No. 17, pp. 5238–5248, 1998.

Williamson et al., "Chemical modification of tissue inhibitor of metallooproteinases–1 and its inactivation by diethyl pyrocarbonate", Biochimica et Biophysica Acta., 1203 (1993) pp. 147–154.

Shofuda et al., "Role of Tissue Inhibitor of Metalloproteinases–2 (TIMP–2) Regulation of Pro–Gelatinase A Activation Catalyzed by Membrane–Type Matrix Metalloproteinase–1 (MT1–MMP) in Human Cancer Cells", J. Biochem. 124, pp. 462–470 (1998).

Miyazaki et al., "Purification and Characterization of a Two–chain Form of Tissue Inhibitor of Metalloproteinases (TIMP) Type 2 and a Low Molecular Weight TIMP–like Protein", The Journal of Biological Chemistry, The Journal of Biological Chemistry, vol. 268, No. 19, Jul. 5, 1993, pp. 14387–14393.

Birkedal–Hansen et al., "Matrix Metalloproteinases: A Review", Critical Reviews in Oral Biology and Medicine, 4(2): 197–250, (1993).

Nagase, "Activation Mechanisms of Matrix Metalloproteinases", Biol. Chem., vol. 378, pp. 151–160, Mar./Apr., 1997.

Miyazaki et al., "Purification and Characterization of Extracellular Matrix–degrading Metalloproteinase, Matrin (Pump–1), Secreted from Human Rectal Carcinoma Cell Line", Cancer Research, 50, 7758–7764, Dec. 15, 1990.

Kinoshita et al., "TIMP–2 Promotes Activation of Progelatinase A by Membrane–type 1 Matrix Metalloproteinase Immobilized on Agarose Beads", The Journal of Biological Chemistry, vol. 273, No. 26, Jun. 26, 1998, pp. 16098–16103.

Higashi et al, "Reactive–site Modified Tissue Inhibitor of Metalloproteinases–2 Inhibits the Cell–Mediated Activation of Progelatinase A", Chemical Abstracts, vol. 131, No. 6, Aug. 9, 1999 (Aug. 9, 1999), Columbus, Ohio, US; abstract No. 70355, XP002142420 & Journal Of Biological Chemistry, vol. 274, No. 15, 1999, pp. 10497–10504, American Society Of Biological Chemists, Baltimore, MD.

* cited by examiner

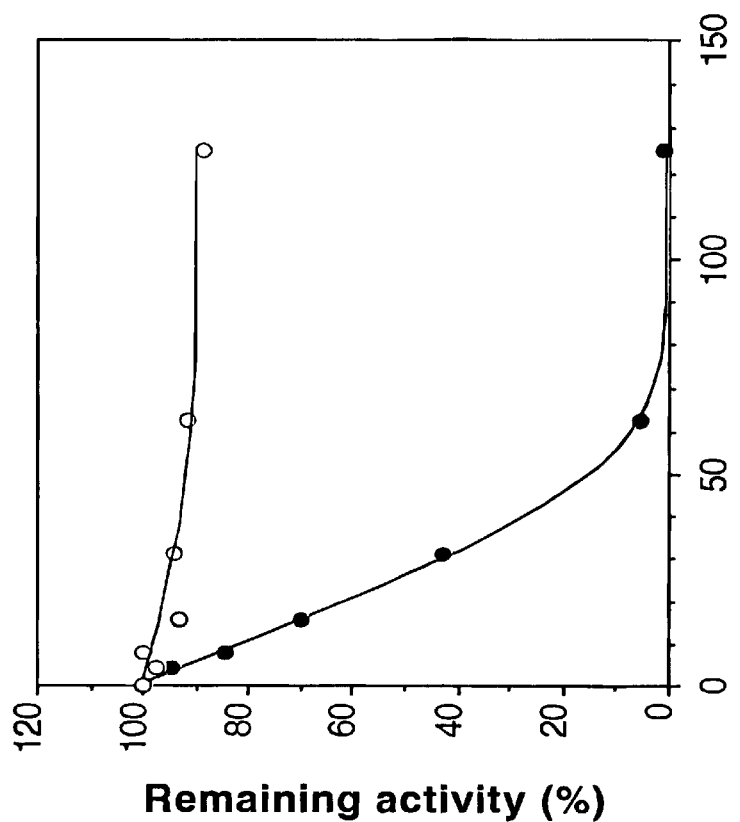
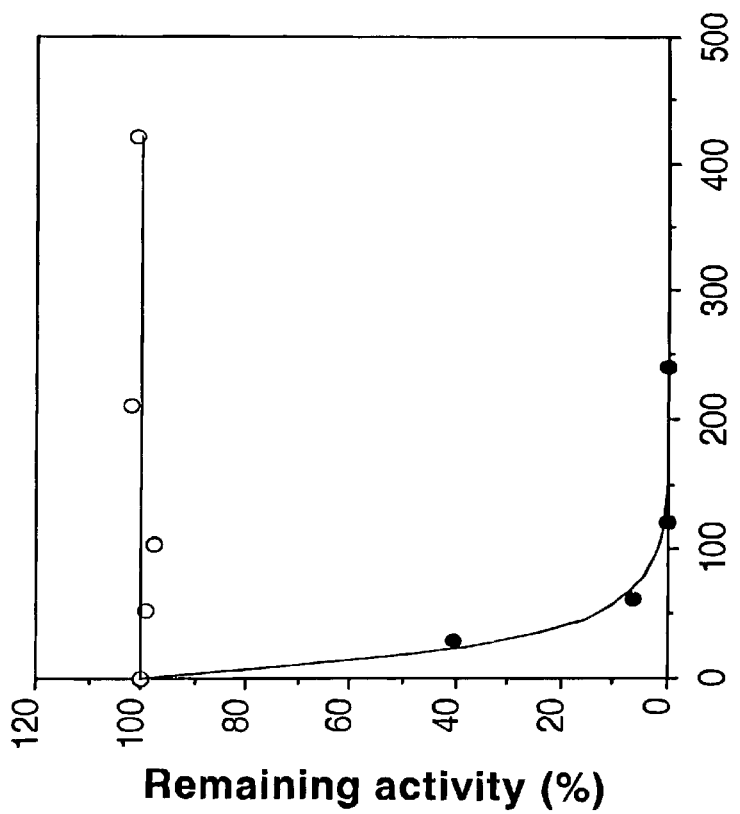

MODIFIED TIMP

BACKGROUND OF THE INVENTION

The present invention relates to novel modified tissue inhibitors of metalloproteinase (hereinafter referred to as "TIMPs").

The subject application claims priority based on the Japanese Patent Application No. 095142/1999. The contents of the Japanese application is hereby incorporated by reference.

Metastasis is a feature of malignant cancer and most life-threatening pathologies and therefore one of the important objects of cancer therapy is to arrest metastasis. In practice, metastasis is palliatively treated by surgery, radiation therapy or chemotherapy, but no therapy can definitively arrest it. However, the mechanism of metastasis has been gradually elucidated in recent years and the breakdown system of extracellular matrix (hereinafter referred to as "ECM") is noted as a reflection of the metastatic potency of cancer.

More specifically, cancer cells begin to grow at the primary location and some of them discontinue adhering to surrounding cells so that they can escape from tumor tissues. However, tumor tissues are surrounded by dense ECM, and cancer cells cannot escape from there only via attack by physical motion without enzymatic breakdown. Metastatic cancer cells begin to move in the tissues by producing an enzyme that breaks down this barrier ECM. To further move to a distant location, cancer cells break vascular walls formed by robust ECM to enter the bloodstream. Then, they adhere to the inner membranes of the vascular walls at the second location, and enzymatically break down the vascular wall ECM again to escape from the vessel and infiltrate tissues by further breaking down surrounding ECM ("SAIBOU KOUGAKU" (Cell Technology), Vol. 17, No. 4, 1998, pp. 523–533).

In such a cascade of processes, breakdown of EMC seems to be most important for studying or diagnosing metastasis of cancer cells. Matrix metalloproteinases (hereinafter referred to as "MMPs") (Docherty, A. J. P., O'Connell, J., Crabbe, T., Angal, S. and Murphy, G. (1992) Trends Biotechnol. 10, 200–207) are zinc-dependent endopeptidases that degrade components of ECM. MMPs play an essential role in tissue remodeling under physiological and pathological conditions such as morphogenesis, angiogenesis, tissue repair and tumor invasion (Docherty, A. J. P. et al., (1992) Trends Biotechnolol. 10, 200–207, supra.; Matrisian, L. M. (1992) Bioessays 14, 455–463; Stetler-Stevenson, W. G., Aznavoorian, S., and Liotta, L. A. (1993) Annu. Rev. Cell Biol. 9, 541–573). Most MMPs are secreted as zymogens and are activated by serine proteases or some activated MMPs.

At present, about twenty MMPs have been discovered, which have characteristic substrate specificities to degrade various collagens, glycoproteins, proteoglycans, etc. MMPs are grouped into several families by their substrate specificities and morphologies. For example, MMP-2 and -9 are also referred to as gelatinase A and gelatinase B, respectively, as members of the gelatinase family having a gelatin as a substrate. MMP-14 to -17 are the membrane-associated type, and belong to the MT-MMP family (membrane type-MMP). MMP-14 to -17 are referred to as MT1-MMP, MT2-MMP, MT3-MMP and MT4-MMP, respectively. Other families are the collagenase family (MMP-1, MMP-8, MMP-13 and MMP-18), stromelysin family (MMP-3 and MMP-10), etc.

The activities of activated MMPs are regulated by a family of specific inhibitors known as tissue inhibitors of metalloproteinases (hereinafter referred to as "TIMPs"). At present, four TIMPs have been identified, which efficiently inhibit MMPs except for MT-MMP. MT-MMP has selectivity in that it is efficiently inhibited by TIMP-2 and TIMP-3, but hardly inhibited by TIMP-1. TIMPs have a structure basically consisting of an N-terminal region and a C-terminal region. The MMP-inhibitory activity exists at the N-terminal region of TIMPs, and even recombinant TIMPs lacking the C-terminal region can inhibit MMPs.

Findings on the Mechanism of MMP-inhibitory Activity of TIMPs

Previous studies proposed hypotheses about the mechanism of MMP-inhibitory activity of TIMPs. For example, the following findings have been obtained about TIMP-2 and TIMP-1.

Among the MMP family, gelatinase A (MMP-2) and gelatinase B (MMP-9) are critical in the invasion of tumor cells across basement membranes because of their strong activity against type IV collagen, a major component of basement membranes (Liotta, L. A. (1986) Cancer Res. 46, 1–7; Collier. I. E., Wilhelm, S. M., Elsen, A. Z., Marmer, B. L., Grant G. A., Seltzer, J. L., Kronberger, A., He, C., Bauer E. A., and Goldberg, G. I. (1988) J. Biol. Chem. 263, 6579–6587; Wilhelm, S. M., Collier, I. E., Marmer, B. L., Eisen, A. Z., Grant G. A., and Goldberg, G. I. (1989) J. Biol. Chem. 264, 17213–17221). Unlike other zymogens of MMPs, progelatinase A is not activated by serine proteases or soluble MMPs and had been reported to be activated by a MMP-like activity on the surface of cancer and fibroblastic cells (Overall, C. M., and Sodek, J. (1990) J. Biol. Chem. 265, 21141–21151; Brown, P. D., Levy, A. T., Margulies, I. M., Liotta, L. A., and Stetler-Stevenson, W. G. (1990) Cancer Res. 50, 6184–6191; Ward, R V., Atkinson, S. J., Slocombe, P. M., Docherty, A. J., Reynolds, J. J., and Murphy, G. (1991) Biochim. Biophys. Acta. 1079, 242–246; Azzam, H. S. and Thompson, E. W. (1992) Cancer Res 52, 4540–4544).

Sato et al. (Sato, H., Takino, T., Okada, Y., Cao, J., Shinagawa, A., Yamamoto, E., and Seiki, M. (1994) Nature 370, 61–65) identified a novel membrane-type MMP, named MT-MMP as an activator of progelatinase A on the cell surface. The cell-mediated activation of progelatinase A includes two steps of processing; MT-MMP-catalyzed cleavage of progelatinase A at a peptide bond between Asn-37 and Leu-38 firstly converts the zymogen into an intermediate form, and then autocatalytic cleavage of an Asn-80-Tyr-81 bond converts the intermediate form into a mature one (Strongin, A. Y., Marmer, B. L., Grant, G. A., and Goldberg, G. I. (1993) J. Biol. Chem. 268, 14033–14039). Several studies suggest that both steps are greatly accelerated by binding of (pro)gelatinase A onto the cell surface, and therefore, the receptor of (pro)gelatinase A on the cell surface is important for the activation. Carboxy-terminal hemopexin-like domain of gelatinase A is reported to be essential for the interaction with the cell-surface receptor (Strongin, A. Y., Marmer, B. L., Grant, G. A., and Goldberg, G. I. (1993) J. Biol. Chem. 268, 14033–14039; Strongin, A. Y., Collier, I., Bannikov, G., Marmer, B. L., Grant, G. A., and Goldberg, G. I. (1995) J. Biol. Chem. 270, 5331–5338).

Recent studies (Brooks, P. C., Silletti, S., von Schalscha, T. L., Friedlander, M., and Cheresh, D. A. (1996) Cell 92, 391–400; Kinoshita, T., Sato, H., Takino, T., Itoh, M., Akizawa, T., and Seiki, M. (1996) Cancer Res. 56, 2535–2538; Pei, D. Q., and Weiss, S. J. (1996) J. Biol. Chem. 271, 9135–9140; Will, H., Atkinson, S. J., Butler, G. S., Smith, B., and Murphy, G. (1996) J. Biol. Chem. 271, 17119–17213; Lichte, A., Kolkenbrock, H., and Tschesche, H. (1996) FEBS Lett. 397, 277–282) suggest that transmembrane domainless variants of MT-MMP convert progelatinase A to the intermediate form but hardly to the mature one. It is also reported that cell-mediated processing of mutant progelatinase A of which active site residue is replaced by site-directed mutagenesis, does not produce the mature form of the mutant (Atkinson, S. J., Crabbe, T., Cowell, S., Ward, R. V., Butler, M. J., Sato, H., Seiki, M., Reynolds, J. J., and Murphy, G. (1995) J. Biol. Chem. 270, 30479–30485; Sato, H., Takino, T., Kinoshita, T., Imal, K., Okada, Y., Stetler-Stevenson, W. G., and Seiki, M. (1996) FEBB Lett. 385, 238–240).

These studies suggest the importance of cell-associated activity of gelatinase A for the conversion of intermediate form of gelatinase A to its mature form.

On the other hand, the crystal structures of complexes of TIMPs and MMPs have also been studied.

The crystal structure of the complexformed between TIMP-1 and stromelysin suggests that the free α-amino group and carbonyl oxygen of $NH_2$-terminal Cys-1 of TIMP-1 coordinate the catalytic zinc atom of stromelysin, thus being involved in the inhibitory action (Gomis-Ruth, F. X., Maskos, K., Betz, M., Bergner, A., Huber, R., Suzuki, K., Yoshida, N., Nagase, H., Brew, K., Bourenkov, G. P., Bartunik, H., and Bode, W. (1997) Nature,389, 77–81). Quite recently, the crystal structure of the complex formed between TIMP-2 and catalytic domain of MT1-MMP was also determined (Fernandez-Catalan, C., Bode, W., Huber, R., Turk, D., Calvete, J. J., Lichte, A., Tschesche, H., and Maskos, K. (1998) EMBO J. 17, 5238–5248). However, the crystal structures of the two MMP-TIMP complexes also indicate that TIMPs have wide range contacts with the corresponding MMPs.

Previously, it had been reported that chemical modification of TIMP-1 with diethyl pyrocarbonate abolishes the inhibitory activity. The modified residues are His-95, His-144 and His-164 of TIMP-1, and the modification of His-95 has been proposed to be responsible for the loss of activity (Williamson, R. A., Smith. B. J., Angal, S., and Freedman, R. B. (1993) Biochim. Biophys. Acta. 1203, 147–154). However, a study based on site-directed mutagenesis has revealed that replacement of His-95 to glutamine does not affect the inhibitory activity of TIMP-1 (Williamson, R. A., Smith, B. J., Angal, S., and Freedman, R. B. (1993) Biochem. Biophys. Acta. 1203, 147–154). Furthermore, the H95Q mutant is still sensitive to the diethyl pyrocarbonate-treatment. So far, there is no explanation for the effect of diethyl pyrocarbonate on the TIMP-1 activity.

Thus, the mechanism of MMP-inhibitory activity of TIMPs has been explained by the formation of complexes between TIMPs and MMPs, and the N-terminal region of TIMPs seemed to be involved in the formation of such complexes. However, the details are unknown and any methods for effectively arresting metastasis of cancer have not been obtained from the explanation of such a mechanism.

SUMMARY OF THE INVENTION

An object of the present invention is to provide a novel modified TIMP. The $NH_2$-terminal α-amino group of the present TIMP is modified with an electron-accepting group to substantially lose the ability to bind to a metalloproteinase.

The modified TIMP of the present invention is preferably a modified TIMP-2.

In the present-invention, said electron-accepting group is preferably a carbamyl group.

The present invention also provides a method of inhibiting the formation of a complex including a TIMP by adding said modified TIMP. The method may be any of in vivo, in vitro or ex vivo method.

In the inhibiting method of the present invention, said-modified TIMP is preferably a modified TIMP-2 and the complex is one including MT-MMP, TIMP-2 and gelatinase A.

Another object of the present invention is to provide a pharmaceutical composition comprising said modified TIMP in combination with a pharmaceutically acceptable carrier.

The pharmaceutical composition of the present invention is used for the inhibition of metastasis of cancer or the inhibition of vascularization.

BRIEF DESCRIPTION OF THE DRAWINGS

FIG. 2. Inhibitory activity of KNCO-treated TIMP-2 forms in matrilysin-bound and matrilysin-unbound fractions. After treatment with KNCO, the partially modified TIMP-2 was separated, using a matrilysin-Sepharose 4B column as described under "Experimental Procedures". Matrilysin (30 nM, panel A) and APMA-activated gelatinase A (80 nM, panel B) were incubated, respectively, with 0.1 mM 3167v at 37° C. for 40 min in the presence of various concentrations of the KNCO-treated TIMP-2 forms in the matrilysin-bound (●) and matrilysin-unbound (○) fractions. All the reaction mixtures contained TBS, 10 mM $CaCl_2$ and 0.01% Brij 35. The amount of 3167v hydrolyzed by enzyme was taken as 100%, and the relative amount of 3167v hydrolyzed by enzyme in the presence of each concentration of the KNCO-treated TIMP-2 forms is shown in ordinate.

DETAILED DESCRIPTION OF THE INVENTION

Figure 1B:
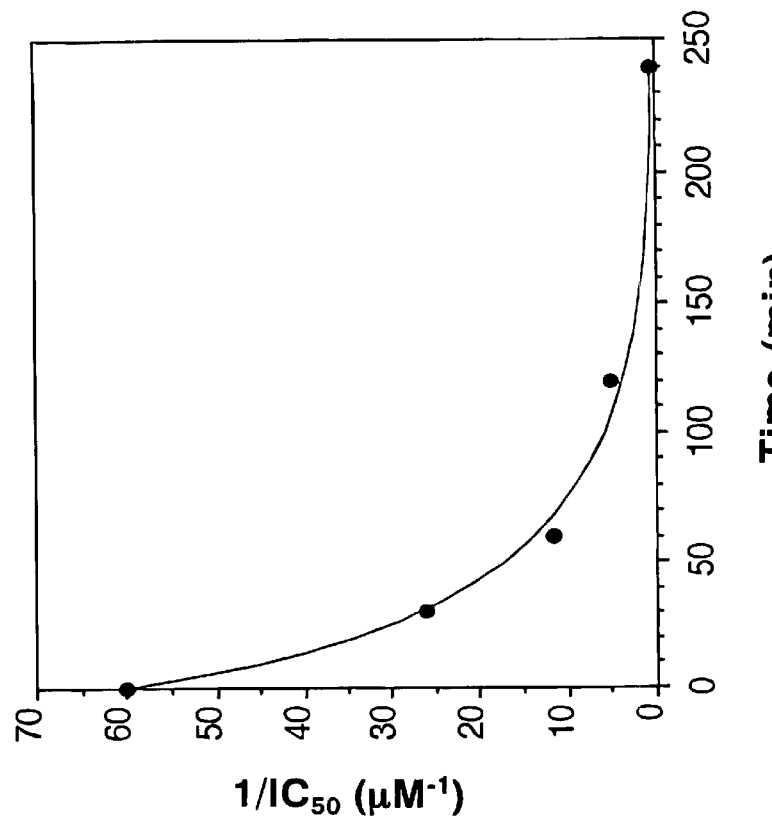
FIG. 1. Effect of KNCO on inhibitory activity of TIMP-2. TIMP-2 (2 μM) was incubated with 0.2 M KNCO in TBS at 37° C. for 0 (●), 30 (○), 60 (▲), 120 (Δ), and 240 (x) min. After incubation, each of the samples was treated with hydroxylamine hydrochloride, and dialyzed against TBS as described under "Experimental Procedures". In panel A, matrilysin (30 nM) was incubated with 0.1 mM 3167v at 37° C. for 40 min in the presence of various concentrations of the KNCO-treated derivatives of TIMP-2. All the reaction mixtures contained TBS, 10 mM $CaCl_2$, and 0.01% Brij 35. The amount of 3167v hydrolyzed by matrilysin was taken as 100%, and the relative amount of 3167v hydrolyzed by matrilysin in the presence of each concentration of the KNCO-treated derivatives of TIMP-2 is shown in ordinate. In panel B, inverse values of $IC_{50}$ obtained in panel A versus the incubation time with KNCO are plotted. $IC_{50}$ represents the concentration of the KNCO-treated derivatives of TIMP-2 that gives a 50% inhibition of the activity of matrilysin.

As a result of careful studies to explain the mechanism of MMP-inhibitory activity of TIMPs and to effectively arrest Invasion and metastasis of cancer and various events caused by invasion of vascular endothelial cells, such as vascularization, we accomplished the present invention, as described more in detail below.

We studied TIMP-2 among TIMPs based on the following hypothesis. The $NH_2$-terminal reactive site of TIMP-2 binds to the active site of MT-MMP to form a protease-inhibitor complex, whereas the COOH-terminal region of TIMP-2 has an affinity for the hemopexin-like domain of gelatinase A. Therefore, it is hypothesized that a complex formed between MT-MMP and TIMP-2 acts as a receptor of progelatinase A. This hypothesis appears to be supported by the finding that overexpressing of MT-MMP results In an accumulation of gelatinase A on the cell surface (Sato, H., Takino, T., Okada, Y., Cao. J., Shinagawa, A., Yamamoto, E., and Seiki, M. (1994) Nature 370, 61–65).

TIMP-2 is a bifunctional regulator of the cell-mediated activation of progelatinase A. Strongin et al. (Strongin, A. Y., Collier, I., Bannikov, G., Marmer, B. L., Grant, G. A., and Goldberg, G. I. (1995) J. Biol. Chem. 270, 5331–5338) demonstrated that small amount of TIMP-2 facilitates the activation of progelatinase A by the MT-MMP-containing cell membrane, whereas excess TIMP-2 strongly inhibits the activation of MT-MMP. This may be because the binding of TIMP-2 to MT-MMP provides a receptor for progelatinase A and also leads to an inhibition of catalytic activity of MT-MMP.

We examined expression levels of gelatinase A, TIMP-2 and three MT-MMPs in human cancer cell lines and found that activation of progelatinase A has a strong inverse correlation only with the level of TIMP-2 secreted into culture medium. This suggests that TIMP-2 is a key regulator of the activation of progelatinase A (Shofuda, K., Moriyama, K., Nishihashi, A., Higashi, S., Mizushima, H., Yasumitsu., H., Miki, K., Sato, H., Seiki, M., and Miyazaki, K. (1998) J. Biochem. (Tokyo) 124, 462–470).

According to the data on the crystal structures of the complexes of TIMPs and MMPs described above, the α-amino group and carbonyl oxygen of the $NH_2$-terminal Cys-1 of both TIMP-1 and TIMP-2 interact with the catalytic zinc of the proteases, suggesting that chelation of the catalytic zinc atom by the $NH_2$-terminal Cys-1 of TIMPs is a common mechanism for the inhibition of MMP activity.

On the foregoing hypothesis, we prepared modified forms of TIMP-2 wherein the $NH_2$-terminal site of TIMP-2 presumed to be involved in binding to MMPs is modified. And, we examined the effects of the modified forms of TIMP-2 on the cell-mediated activation of progelatinase A. As a result, we found that treatment of TIMP-2 with cyanate ion led to loss of inhibitory activity toward matrilysin or gelatinase A. Structural and functional analyses of the modified forms of TIMP-2 showed that the loss of inhibitory activity results from carbamylation of the α-amino group of $NH_2$-terminal Cys-1 of TIMP-2 (Examples).

Accordingly, the present invention provides modified TIMPs wherein the $NH_2$-terminus of a TIMP involved in binding to MMPs is modified to substantially lose the ability to bind to MMPs.

As described above, four types of TIMPs have already been discovered and designated as TIMP-1 to TIMP-4. Their amino acid sequences are shown as SEQ. ID NOs. 1 to 4 in the Sequence Listing. Each type Is produced as a precursor, which turns into a mature form after cleavage of the signal sequence. Cleavage of the signal sequence occurs between alanine and cysteine in each type. Namely, cleavage occurs between the amino acid residues 23 and 24 in TIMP-1, 26 and 27 in TIMP-2, 23 and 24 in TIMP-3, and 29 and 30 in TIMP-4. Therefore, the mature form of each type has a cysteine residue at the N-terminus.

TIMPs can be purified from materials such as conditioned medium of the T98G human glioblastoma cell line, HT1080 human fibrosarcoma cell line, etc. using a known method (Miyazaki, K., Funahashi, K., Numata, Y., Koshikawa, N., Akaogi, K., Kikkawa, Y., Yasumitsu, H., and Umeda, M. (1993) J. Biol. Chem. 268, 14387–14393; and Collier, I. E., Wilhelm, S. M., Eisen, A. Z., Marrer, B. L., Grant G. A., Seltzer, J. L., Kronberger, A., He, C., Bauer, E. A., and Goldberg, G. I. (1988) J. Biol. Chem. 263, 6579–6587).

Alternatively, they can be produced by a genetic engineering method by referring their known amino acid sequences as shown in Sequence Listing. Methods for producing a protein by a genetic engineering method are well known to those skilled in the art, so that those skilled in the art can obtain TIMPs on the basis of the specification.

Modified TIMPs of the present invention are preferably modified forms of TIMP-2. However, modified TIMPs of the present invention are not limited to a specific type of TIMP, but also include modified forms of other types such as TIMP-1. The amino acid sequences shown as SEQ ID NOs. 1 to 4 in Sequence Listing also show high homology especially in the sequences of the $NH_2$-terminal regions. Moreover, the $\alpha$-amino group and carbonyl oxygen of the $NH_2$-terminal Cys-1 of both TIMP-1 and TIMP-2 in the complexes with MMPs seem to interact with the catalytic zinc of the proteases as described above, suggesting that chelation of the catalytic zinc atom by the $NH_2$-terminal Cys-1 of TIMPs is a common mechanism for the inhibition of MMP activity. This indicates that any TIMP substantially loses the ability to bind to MMPs by modifying the $NH_2$-terminus.

In the present invention, the free $NH_2$-terminus of a mature TIMP is modified as described above. Any known electron-accepting groups may be used for the modification. For example, non-limiting examples are carbamyl, acetyl, amidino, trinitrophenyl groups or the like. A carbamyl group is preferred.

Modification of the $NH_2$-terminus with an electron-accepting group can be made by any known method. When modification is made with a carbamyl group, for example, a reaction takes place at first with KNCO in aqueous solution at 20° C. to 40° C., preferably 25° C. to 37° C. for 10 minutes to 5 hours, preferably 20 minutes to 30 minutes. Suitable buffers are Tris-HCl, Hepes-sodium, phosphate buffer, etc. The pH ranges from 7.0 to 8.5. Then, a salt of hydroxylamine such as hydroxylamine hydrochloride is added to terminate the reaction, whereby the amount of the carbamyl group introduced can be controlled. The reaction takes place at 10° C. to 25° C., preferably 20° C. to 25° C. for 30 minutes to 2 hours, preferably 60 minutes to 2 hours.

Then, the modified TIMP with an electron-accepting group introduced can be separated from unmodified TIMP by affinity column or the like. Suitable materials to be immobilized to the affinity column carrier are those capable of binding only to the reactive NH, terminal site of each TIMP, such as matrilysin, stromelysin, etc. for TIMP-2.

Figure 7A:
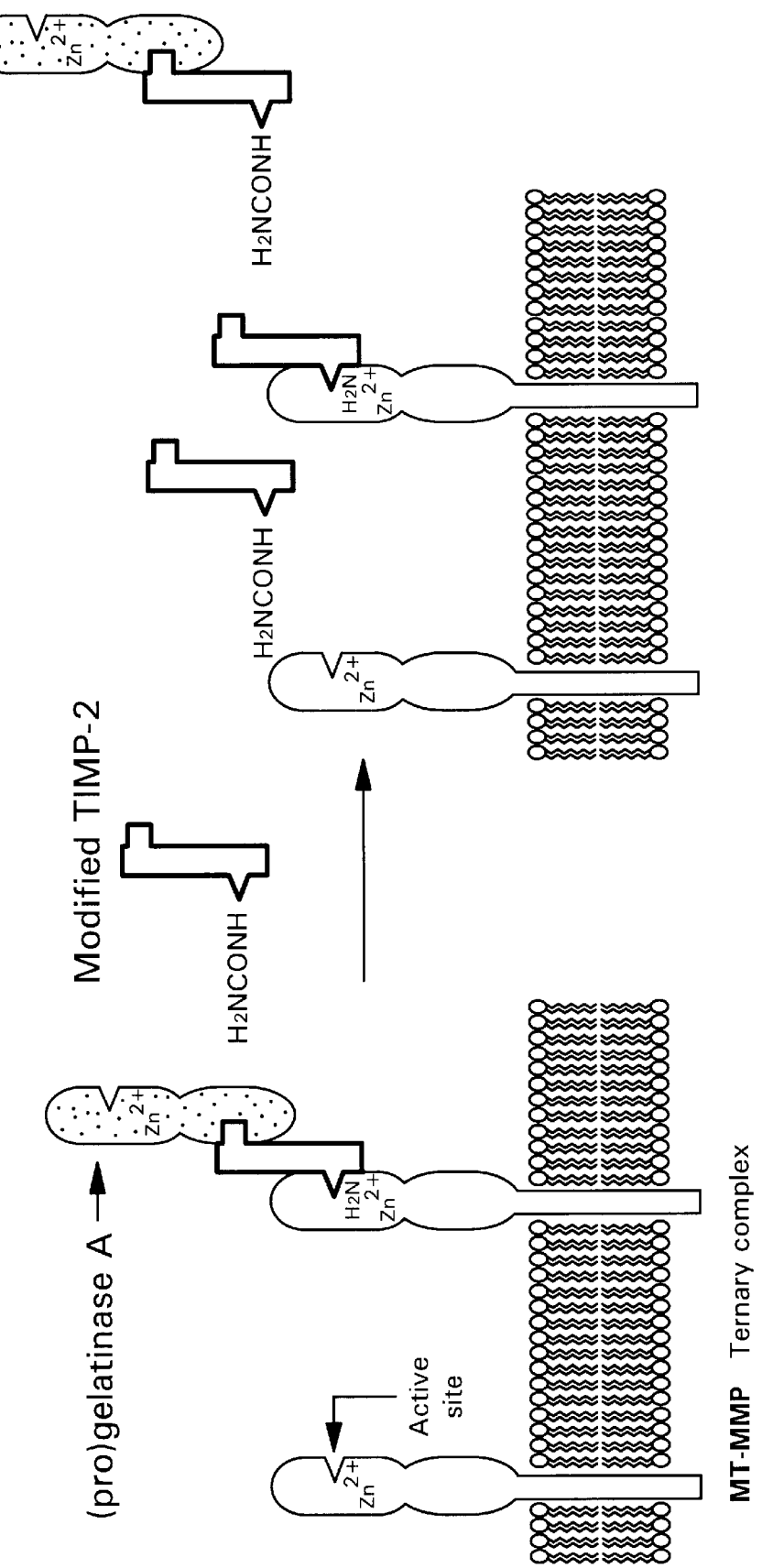
FIG. 7. Hypothetical model for inhibitory effects of modified TIMP-2 and native TIMP-2 on formation of the ternary complex consisting of MT-MMP, TIMP-2 and (pro) gelatinase A. In panel A, the modified TIMP-2 inhibits the formation of the ternary complex consisting of MT-MMP, TIMP-2 and (pro)gelatinase A by competing for the hemopexin-like domain of (pro)gelatinase A. The modified TIMP-2 can not interact with the active site of MT-MMP. In panel B, an excess amount of native TIMP-2 inhibits the formation of the ternary complex by occupying both the active site of MT-MMP and the hemopexin-like domain of (pro)gelatinase A. $H_2N$, the α-amino group of $NH_2$-terminal Cys-1 of TIMP-2; $H_2NCONH$, the carbamylated α-amino group of $NH_2$-terminal Cys-1 of TIMP-2; $Zn^{2+}$, catalytic zinc atom of metalloproteinases.

The modified TIMPs of the present invention, thus obtained, cannot bind to, and therefore, cannot form a complex with MMPs, because it has been modified at the $NH_2$ terminus. For example, the modified TIMP-2 bearing a single carbamylated $\alpha$-amino group had no affinity for matrilysin in the Examples described below in the present specification. Without wishing to be bound to any theory, it is thought that modification of the terminal $NH_2$ of TIMP-2 with an electron-accepting group may lead to a reduction of basicity of the $N\alpha$ nitrogen of the amino group, which makes it unable for the $N\alpha$ nitrogen to coordinate with the catalytic zinc atom of MMPs, thereby abolishing the inhibitory activity of TIMP-2 (FIG. 7A).

Figure 7B:
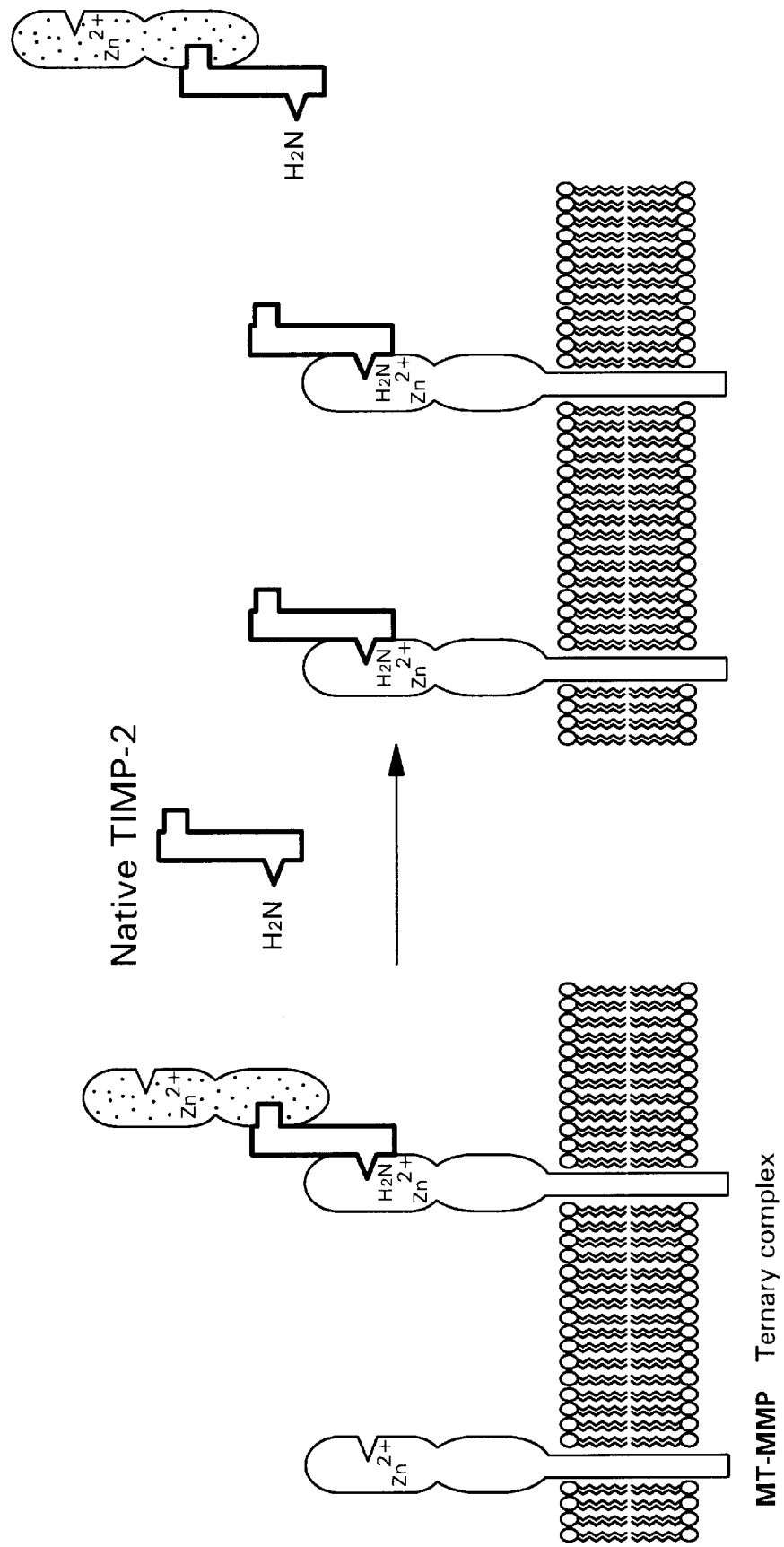

On the other hand, the C-terminal side of modified TIMPs of the present invention is not modified. Therefore, a feature of the present invention is that the reaction for which the C-terminal region of TIMPs is responsible is not inhibited. For example, TIMP-1 and TIMP-2 are known to also form complexes with precursor (pro) MMPS, i e., TIMP-1 binds to precursor MMP-9 and TIMP-2 binds to progelatinase A (precursor MMP-2) by the mutual affinity between their C-terminal regions (Birkedal-Hansen, H., Moore, W. G., Bodden, M. K. et al.: Crit. Rev. Oral Biol. Med. 4, 197–250 (1993); Nagae, H.: Biol. Chem. 378. 151–160 (1997)). Namely, TIMP-2 is presumed to bind to MT1-MMP at the N-terminal region and bind to progelatinase A at the C-terminal side to form a ternary complex. A model was proposed to demonstrate that the formation of said ternary complex is necessary for conversion of progelatinase A into active gelatinase A (FIG. 7B).

Figure 5:
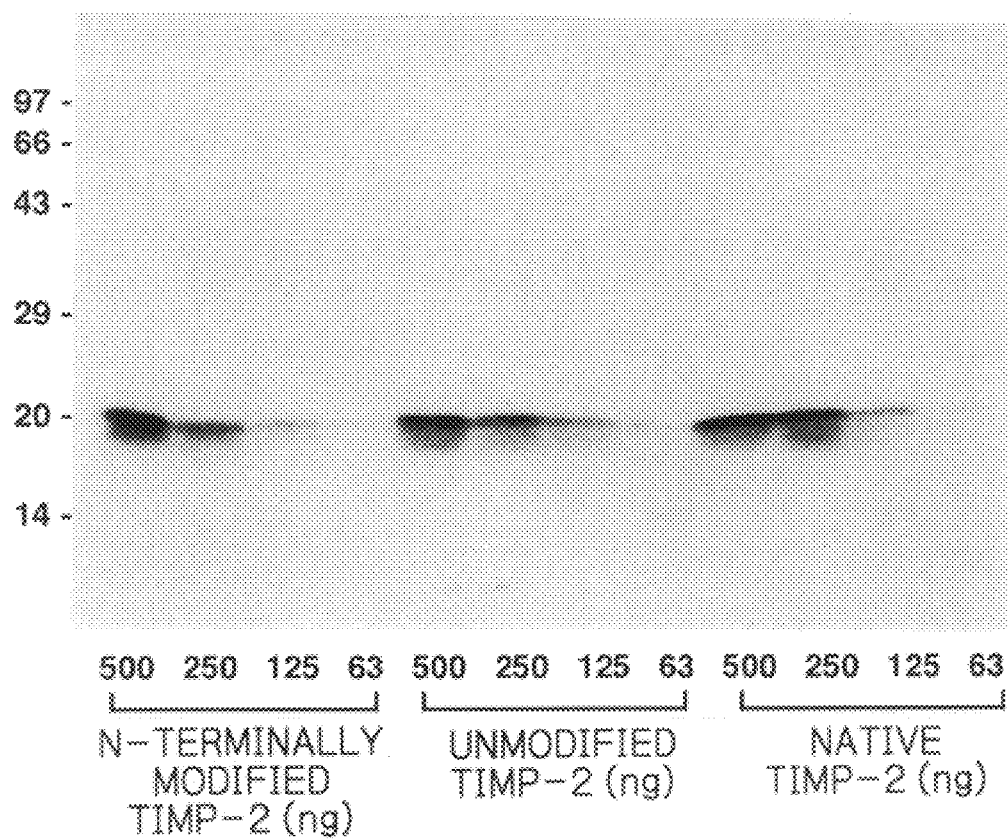
FIG. 5. Progelatinase A binding ability of KNCO-treated TIMP-2 forms in matrilysin-bound and matrilysin-unbound fractions. The indicated amounts of the KNCO-treated TIMP-2 forms in the matrilysin-unbound fraction (N-terminally modified TIMP-2) and matrilysin-bound fraction (unmodified TIMP-2), and native TIMP-2 were subjected to ligand blotting analysis as described under "Experimental Procedures". Ordinate, molecular size in kDa.

Modified TIMPs of the present invention cannot bind to MMPs because the terminal $NH_2$ is modified, e.g. a modified TIMP-2 cannot bind to MT1-MMP, but can bind to progelatinase A because the C-terminus is not modified (FIG. 5). Therefore, it competes with native TIMP-2 for binding to progelatinase A, but does not bind to MT1-MMP, thus inhibiting the formation of a complex including the TIMP. As a result, reactions promoted by the formation of such a TIMP complex are controlled or inhibited. However, the enzymatic activity function of the MMP itself to which the $NH_2$ terminus binds is not affected. For example, a modified TIMP-2 of the present invention can inhibit the activation of progelatinase A without inhibiting the catalytic activity of MT1-MMP (FIG. 7A). Thus, the modified TIMP-2 provides a useful tool to distinguish the protease activity itself of MT1-MMP from the function of promoting the activation of progelatinase A by binding to the TIMP to form a complex.

The present invention also provides pharmaceutical compositions comprising a modified TIMP of the present invention in combination with a pharmaceutically acceptable carrier.

Pharmaceutical compositions of the present invention are useful for inhibiting metastasis of cancer and vascularization for which MMPs are responsible, and for preventing or treating diseases associated therewith. Specifically, they are especially useful for preventing or treating metastasis of cancer of the stomach, colon, lung, head and neck, brain tumor, breast, thyroid, prostate, ovary, pancreas, etc., and vascularization or other conditions associated therewith.

Compositions of the present invention contain a therapeutically effective amount of a modified TIMP of the present invention in admixture with a pharmaceutically acceptable carrier. Compositions of the present invention can be administered systemically or topically and orally or parenterally, such as intravenously, subcutaneously or intramuscularly.

For oral administration, known desired dosage forms such as tablets, powders, liquids, etc. can be used. For preparing pharmaceutical formulations, known desired pharmaceutical auxiliaries such as excipients, diluents, lubricants, binders, flow aids, disintegrating agents surfactants, etc. can be used.

Parenterally administrable TIMP protein solutions can be prepared taking into account the pH, isotonicity, safety or the like within the scope of those skilled in the art.

The dosage regimen of compositions of the present invention can be selected by an attending physician according to a variety of factors influencing the pharmaceutical effects such as the nature and/or severity of the condition, weight, sex and diet of the patient, the time of administration and other clinical effects. Those skilled in the art can determine the dose of compositions of the present invention based on these factors.

The following examples are only for the purpose of illustrating but not limiting the present invention. The scope of the present invention should be determined from the claims. Those skilled in the art can readily add modifications or changes on the basis of the description of the specification.

EXAMPLES

The examples described below were performed according to the following "Experimental Procedures".

Experimental Procedures

Materials

The sources of materials used were as follows (SEQ. ID. No. 65): 3167-v ((7-methoxycoumarin-4-yl) acetyl-Arg-Pro-Lys-Pro-Tyr-Ala-norvalyl-Trp-Met-N$\epsilon$-(2,4-dinitrophenyl)-lysine amide) from Peptide Institute, Inc. (Osaka, Japan): potassium cyanate from Wako Pure Chemical Industries (Osaka); p-aminophenyl mercuric acetate (APMA) from Tokyo Kasei (Tokyo, Japan); CNB$\gamma$-activated Sepharose 4B from Pharmacia Fine Chemicals (Uppsala, Sweden); Ultrasphere ODS 5U (2.0×150 mm) from Beckman (Fullerton, Calif.). Bovine pancreatic trypsin treated with N-tosyl-L-phenylalanine chloromethyl ketone was purchased from Worthington (Freehold, N.J.); the plant lectin concanavalin A (type IV, substantially free of carbohydrates) from Sigma (St. Louis, Mo.); gelatin from Difco (Detroit, Mich.). Recombinant human matrilysin was a product of Oriental Yeast Co., Ltd. (Shiga, Japan). All other chemicals were analytically or commercially available.

Proteins

TIMP-2-free and TIMP-2-bound forms of progelatinase A were separately purified from the conditioned medium (hereinafter referred to as "CM") of the T98G human glioblastoma cell line, as described previously (Miyazaki, K., Funahashi, K., Numata, Y., Koshikawa, N., Akaogi, K., Kikkawa, Y., Yasumitsu, H., and Umeda, M. (1993) J. Biol. Chem. 268, 14387–14393). TIMP-2 was purified from the TIMP-2-bound progelatinase A using a SynChropak RP-4 reverse-phase column (SynChrom; Lafayette, Ind.) according to the method of Coolier et al. (Collier, I. E., Wilhelm, S. M., Eisen, A. Z., Marmer, B. L., Grant G. A., Seltzer, J. L., Kronberger, A., He, C., Bauer, E.A., and Goldberg. G. I. (1988) J. Biol. Chem. 263, 6579–6587). Rabbit antiserum against progelatinase A was prepared by a known method.

Chemical Modification of TIMP-2 with KNCO

50 $\mu$l of 1.0 M KNCO was added to 200 $\mu$l of a protein solution, which contained 500 pmol of TIMP-2 in 50 mM Tris-HCl (pH 7.5) containing 0.1 M NaCl and 0.01% NaN$_3$ (Tris-buffered saline; TBS). The mixture was incubated at 37° C. for 0, 30, 60, 120 and 240 min. After incubation, 50 $\mu$l of each sample taken from the reaction mixture was mixed with 20 $\mu$l of 1.0 M hydroxylamine hydrochloride (pH 8.0) and incubated at 25° C. for 1 h to terminate the modification reaction. The resultant reaction mixtures were dialyzed against TBS at 4° C.

Assay of Inhibitory Activity of TIMP-2 After Chemical Modification

After modification of TIMP-2 under various conditions, various concentrations of the modified TIMP-2 were incubated with matrilysin (33 nM) in 90 $\mu$l of TBS containing 10 mM CaCl$_2$ and 0.01% Brij 35 at 37° C. for 15 min. The mixtures were added with 10 $\mu$l of 1 mM 3167v, and further incubated for 40 min. The reaction was terminated by adding 100 $\mu$l of 0.1 M EDTA (pH 7.5). The amounts of 3167v hydrolyzed by matrilysin were measured fluorometrically with excitation at 360 nm and emission at 460 nm. The amount of 3167v hydrolyzed without enzyme was subtracted from the total amount of the hydrolyzed substrate.

TIMP-2 (150 $\mu$g) was incubated with 0.2 M KNCO in 500 $\mu$l of TBS at 37° C. for 25 min. This treatment resulted in a 50% reduction of inhibitory activity of TIMP-2.

Separation of Active an Inactive TIMP-2 After Partial Carbamylation

The KNCO-treated TIMP-2 sample was further incubated with 0.2 M hydroxylamine hydrochloride at 25° C. for 1 h, and then dialyzed extensively against TBS containing 10 mM CaCl$_2$ at 4° C. To separate inactive TIMP-2 from active TIMP-2, the reaction mixture was applied to a matrilysin-Sepharose 4B column in which 100 $\mu$g of matrilysin had been coupled to 500 $\mu$l of CNBr-activated Sepharose 4B, and the flow-through fraction containing inactive TIMP-2 was collected. After washing the column with TBS containing 10 mM CaCl$_2$, the adsorbed sample (active TIMP-2) was eluted with TBS containing 4 M guanidine hydrochloride and 20 mM EDTA. After the elution, the column was washed sequentially with TBS containing 10 mM CaCl$_2$ plus 50$\mu$M ZnCl$_2$ and with TBS containing 10 mM CaCl$_2$ to renature the immobilized matrilysin. The TIMP-2 samples in the flow-through and eluted fractions were separately dialyzed against phosphate-buffered saline.

Inhibition Assay of Gelatinase A Activity by Modified TIMP-2

TIMP-2-free form of progelatinase A was activated by incubating with 1 mM APMA at 37° C. for 1 h as described previously (Miyazaki, K., Funahashi, K., Numata, Y., Koshikawa, N., Akaogi, K., Kikkawa, Y., Yasumitsu, H., and Umeda, M. (1993) J. Biol. Chem. 268, 14387–14393). The activated gelatinase A (89 nM) was incubated with various concentrations of the KNCO-treated derivatives of TIMP-2 in 90 $\mu$l of TBS containing 10 mM CaCl, and 0.01% Brij 35 at 37° C. for 15 min. The mixtures were added with 10 $\mu$l of 1 mM 3167v, and further incubated for 40 min. The reaction was terminated by adding 100 $\mu$l of 0.1 M EDTA (pH 7.5). The amounts of hydrolyzed 3167v were measured as described above.

Reduction and S-Carboxyamidamothylation of KNCO-Treated TIMP-2 Forms in Matrilysin-Bound and Matrilysin-Unbound Each of the KNCO-treated TIMP-2 forms in matrilysin-bound and matrilysin-unbound fractions (10 $\mu$M) was incubated with 100 mM dithiothreitol in TBS containing 4 M guanidine hydrochloride and 20 mM EDTA at 50° C. for 30 min. After incubation, the samples were transferred to a container of ice water and further incubated with 240 mM iodoacetamide. After 2 h, the samples were dialyzed against TBS.

Cell Culture and Preparartion of CM and Cell Lysates

HT1080 fibrosarcoma cell line was grown to semi-confluency in a 1:1 mixture of Dulbecco's modified Eagle's medium and Ham's F12 medium (Gibco; Grand Island, N.Y.), DME/F12, supplemented with 10% fetal calf serum (FCS). The cells were rinsed three times with serum-free DME/F12, and the culture was further continued in the presence of various concentrations of TIMP-2 or modified TIMP-2 and a fixed concentration of concanavalin A (100 $\mu$g/ml) in serum-free DME/F12. After 24h, the resultant CM was collected, clarified by centrifugation, and dialyzed against distilled water at 4° C. The sample was then lyophilized and dissolved in a small volume of a sodium dodecyl sulfate-sampling buffer consisting of 50 mM Tris-HCl (pH 6.8), 2% sodium dodecyl sulfate and 10% glycerol. By these procedures, the initial CM was concentrated 20-fold. To prepare cell lysates, the cells were rinsed three times with phosphate-buffered saline, and then dissolved in a small volume of the sodium dodecyl sulfate-sampling buffer.

Ligand Blotting Analysis

TIMP-2 or modified TIMP-2 was subjected to sodium dodecyl sulfate-polyacrylaride gel electrophoresis, under non-reducing condition. After the electrophoresis, the proteins on the gel were transferred onto a nitrocellulose membrane, using a Bio-Rad Mini Trans-Blot apparatus (Richmond, Calif.). The membrane was blocked with TBS containing 5% skim milk at room temperature for 12 h, washed with TBS containing 0.05% Tween 20, 10 mm $CaCl_2$ and 0.19 bovine serum albumin (TBS-Tween), and then incubated at room temperature with progelatinase A (5 $\mu$g/ml) in TBS-Tween. After 3 h, the membrane was washed with TBS-Tween and incubated for 3 h with an anti-progelatinase A antiserum, which had been diluted 1000-fold with TBS-Tween. After washing with TBS-Tween, the membrane was incubated with a 1600-fold diluted biotinylated anti-rabbit IgG antibody (Vector Laboratories; Burlingame, Calif.), washed with TBS-Tween, and then incubated with avidin-alkaline phosphate (Vector) at room temperature for 1 h. The membrane was washed extensively and then incubated in a reaction mixture containing 5-bromo-4-chloro-3-indolylphosphate and nitro blue tetrazolium to develop a colored product on the membrane.

Gelatin Zymography

Zymography was carried out on 10% polyacrylamide gels containing 1 mg/ml of gelatin, as described by Miyazaki et al. (Miyazaki, K., Hattori, Y., Umenishi, F., Yasumitsu, H., and Umeda, M. (1990) Cancer Res. 50, 7758–7764).

Amino-terminal Sequence Analysis

Samples were analyzed on an Applied Biosystems 477A gas-phase sequencer. Phenylthiohydantoin derivatives were detected using an Applied Biosystems 120A PTH analyzer with an on-line system.

Mass Spectrometric Analysis

Tryptic peptides of TIMP-2 (10 pmol/$\mu$l) were mixed together with an equal volume of $\alpha$-cyano-4-hydroxycinnamic acid solution (10 mg of $\alpha$-cyano-4-hydroxycinnamic acid was dissolved in 1 ml of 50% acetonitrile containing 0.1% trifluoroacetic acid). The sample/matrix solution was dropped onto a sample plate for matrix-assisted laser desorption ionization time of flight mass spectrometry, then dried under ambient conditions. A mass spectrum was obtained on a Voyager-DE™ STR system (PerSeptive Biosystems, Inc.; Framingham, Mass.).

EXAMPLES

Effect of KNCO-treatment of TIMP-2 on the Inhibitory Activity

Figure 1A:
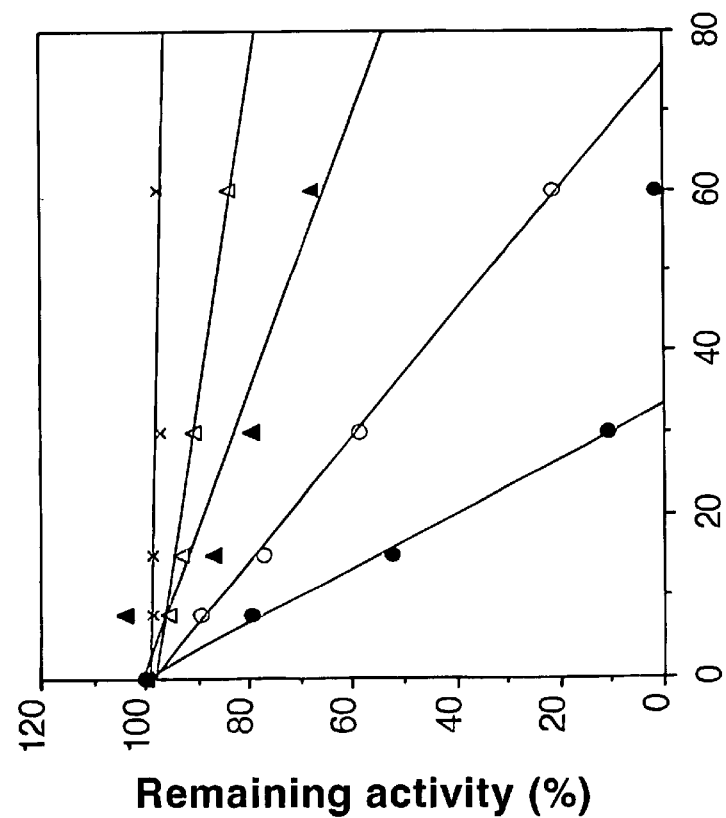

The recently determined crystal structure of the complex formed between TIMP-1 and stromelysin suggests that the $\alpha$-amino group of $NH_2$-terminal Cys-1 of TIMP-1 binds to the catalytic zinc atom at the active site of stromelysin, thus playing an essential role in the inhibitory action of TIMP-1 (Gomis-Ruth, F. X., Maskos, K., Betz, M., Bergner, A., Huber, R., Suzuki, K., Yoshida, N., Nagase, H., Brew, K., Bourenkov, G. P., Bartunik H., and Bode, W. (1997) Nature 389, 77–81). As the structure of $NH_2$-terminal region of TIMP-2 is homologous to that of TIMP-1, the $\alpha$-amino group of Cys-1 of TIMP-2, corresponding to that of TIMP-1 may be critical for the inhibitory activity of TIMP-2. To examine this possibility, we attempted to carbamylate the $\alpha$-amino group of Cys-1 by treating TIMP-2 with KNCO under various conditions, and the modified derivatives of TIMP-2 were examined for their abilities to inhibit the matrilysin-catalyzed hydrolysis of 3167v. As shown in FIG. 1A, the incubation of TIMP-2 with. KNCO led to an increase in the $IC_{50}$ value of the inhibition, where $IC_{50}$ represents the concentration of the modified derivatives of TIMP-2 giving a 50% inhibition of the activity of matrilysin. When the inverse values of the $IC_{50}$ versus incubation time with KNCO were plotted, the $1/IC_{50}$ value diminished with increasing time of Incubation with KNCO, and 50% reduction of the $1/IC_{50}$ value was observed when the incubation time was 25 min (FIG. 1B). The inhibitory activity of TIMP-2 was abolished after 4 h incubation with KNCO.

Separation of Active and Inactive Fractions After Partial Modification of TIMP-2

As described under "Experimental Procedures", TIMP-2 was treated with 0.2 M KNCO at 37° C. for 25 min. This modification led to a loss of 50% inhibitory activity of TIMP-2 (FIG. 1). The partially modified TIMP-2 was then separated on a matrilysin-Sepharose 4B column. After the separation, matrilysin-bound and matrilysin-unbound fractions contained almost the same amount of protein (data not shown), suggesting that about 50% of the modified TIMP-2 before separation had essentially no affinity for matrilysin. The matrilysin-bound fraction and native TIMP-2 showed comparable abilities to inhibit the matrilysin-catalyzed hydrolysis of 3167v (FIG. 2A). In contrast, the matrilysin-unbound fraction had no inhibitory activity. The matrilysin-unbound fraction was also inactive against APMA-activated gelatinase A (FIG. 2B). These data are consistent with the view that the treatment of TIMP-2 with KNCO leads to a modification of the terminal $NH_2$ of TIMP-2, thus preventing the formation of the protease-inhibitor complex.

Determination of the Sit of Modification Responsible for the Loss of Inhibitory Activity of TIMP-2

Figure 3A:
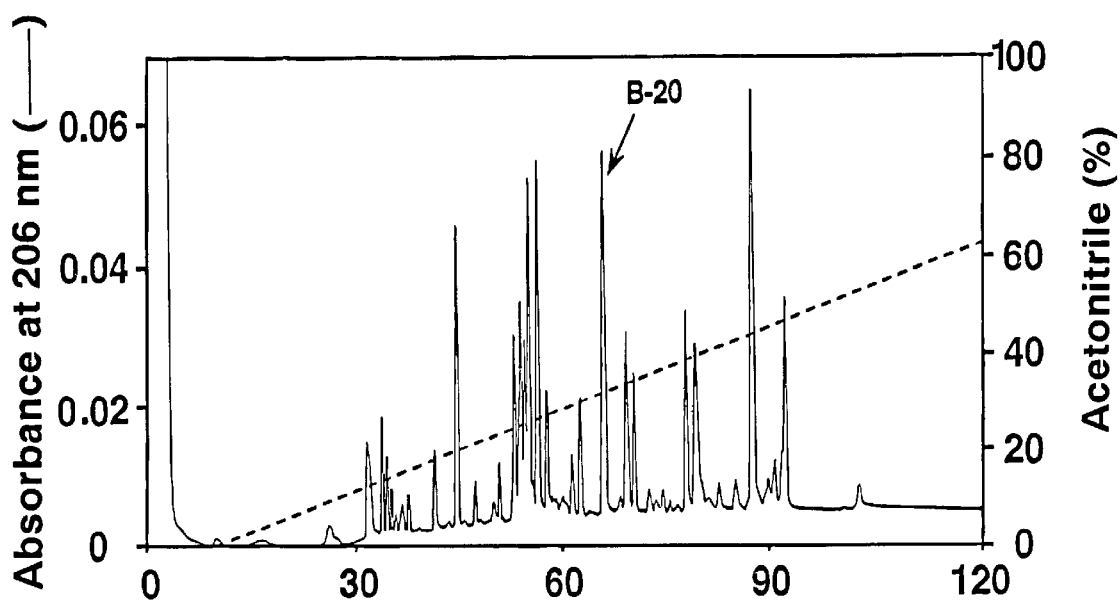
FIG. 3. HPLC separation of tryptic peptides of XNCO-treated TIMP-2 forms in matrilysin-bound and matrilysin-unbound fractions. Each of the KNCO-treated TIMP-2 forms in the matrilysin-bound (panel A) and matrilysin-unbound (panel B).fractions was reduced and S-carboxamidomethylated as described under "Experimental Procedures", and then digested with trypsin in an enzyme to substrate ratio of 1:100 (w/w) at 37° C. for 24 h. The digest was applied to an Ultrasphere ODS 5U column (2.0×150 mm) and eluted at a flow rate of 0.5 ml/min with a linear gradient of acetonitrile containing 0.05% trifluoroacetic acid. The column eluate was monitored at 206 nm (solid lines), and the broken line shows the percentage of acetonitrile in the elution medium.
Figure 3B:
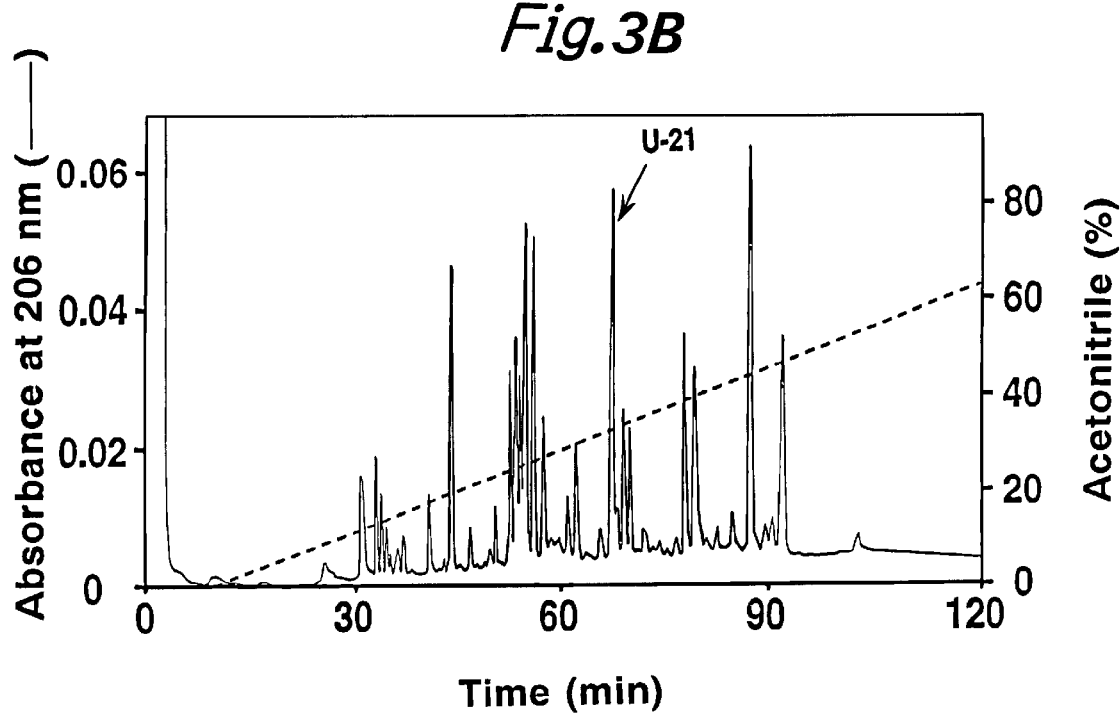
Figure 4A:
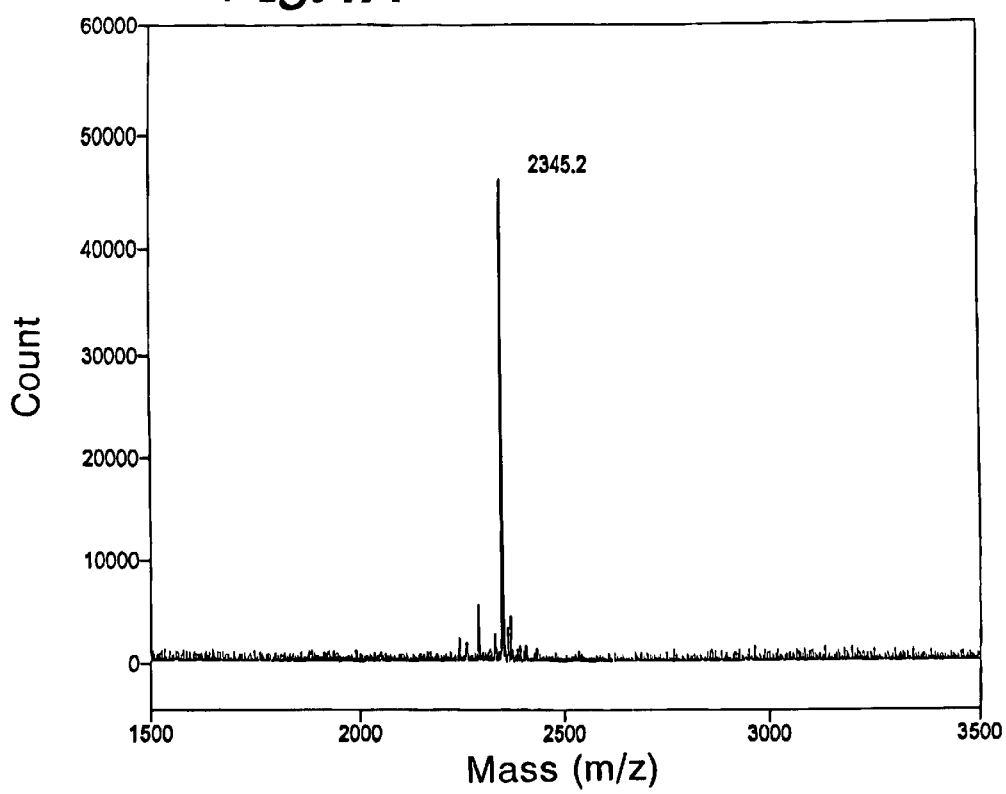
FIG. 4. Mass spectra of B-20 and U-21. Peaks B-20 (panel A) and U-21 (panel 5) obtained from the ODS column were subjected to matrix-assisted laser desorption ionization time of flight mass spectrometry, using 10 mg/ml α-cyano-4-hydroxycinnamic acid/50% acetonitriule/0.1% trifluoroacetic acid as the matrix solution.
Figure 4B:
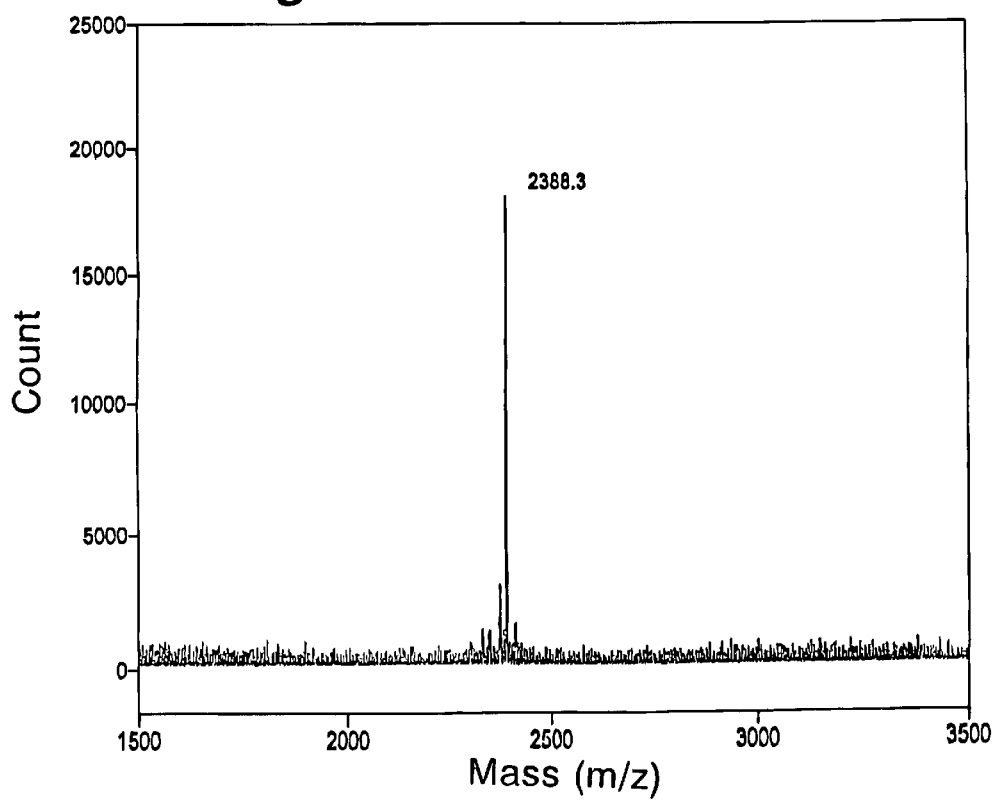

To determine the site of modification responsible for the loss of inhibitory activity, the samples in matrilysin-bound and matrilysin-unbound fractions were reduced and S-carboxamidomethylated and then subjected to tryptic digestion, after which the digests were separated by reverse phase HPLC. The differences observed between the two elution profiles were only peaks B-20 and U-21 from the matrilysin-bound and matrilysin-unbound fractions, respectively (FIGS. 3A and B). The mass spectrometric analyses of the peptides (FIGS. 4A and B) showed that the molecular masses of B-20 and U-21 were 2345.22 and 2388.26, respectively. Based on the determined molecular mass, B-20 is assigned as the peptide corresponding to residues 1–20 of human TIMP-2. On the other hand, the difference of the molecular masses between B-20 and U-21 corresponds to the mass of a carbamyl adduct, suggesting that U-21 is a peptide corresponding to residues 1–20 of TIMP-2 bearing a single carbamylated amino group.

Furthermore, the sequence corresponding to residues 1–19 of TIMP-2 was determined in the $NH_2$-terminal sequence analysis on B-20, where each of the residues 1, 3 and 13 was detected as a phenylthiohydantoin-derivative of S-carboxamidomethylcysteine. However, no phenylthiohydantoin-derivative of amino acid was detected in the $NH_2$-terminal sequence analysis of U-21. These results indicate that B-20 and U-21 are peptide derived from the $NH_2$-terminal region of TIMP-2 corresponding to residues 1–20, and that the $\alpha$-amino group of Cys-1 of U-21 is carbamylated.

These results also suggest that the carbamylation of the $\alpha$-amino group of $NH_2$-terminal Cys-1 of TIMP-2 leads to the inactivation of TIMP-2.

Effect of KNCO-treatment of TIMP-2 on the Progelatinase A-binding Ability

In addition to the MMP-inhibitory activity, TIMP-2 also has the ability to interact with the hemopexin-like domain of progelatinase A. To examine whether the carbamylation of TIMP-2 affects the progelatinase A-binding ability, the matrilysin-bound and matrilysin-unbound fractions of KNCO-treated TIMP-2 and native TIMP-2 were tested for their progelatinase A-binding abilities, using the ligand-blotting analysis as described under "Experimental Procedures". As shown in FIG. 5, native TIMP-2 and the KNCO-treated TIMP-2 in the matrilysin-unbound fraction and that in matrilysin-bound one had comparable abilities to bind with progelatinase A, suggesting that the carbamylation of TIMP-2 has essentially no effect on the interaction with progelatinase A.

Figure 6A:
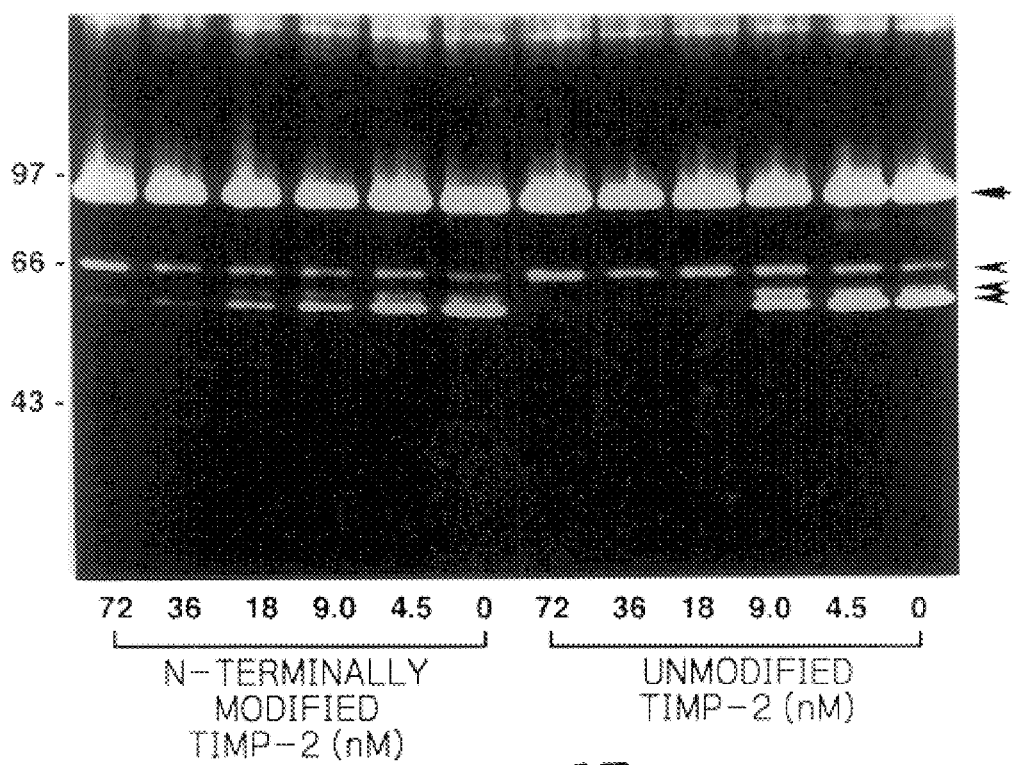
FIG. 6. Effects of N-terminally modified and unmodified TIMP-2 on processing of progelatinase A in lysates and CM of concanavalin A-stimulated HT1080 cells. HT1080 cells were incubated in serum-free medium with the indicated concentrations of the KNCO-treated TIMP-2 forms in the matrilysin-unbound fraction (N-terminally modified TIMP-2) and matrilysin-bound fraction (unmodified TIMP-2) and a fixed concentration (100 μg/ml) of concanavalin A. Cell lysates (panel A) and CMs (panel B) were prepared from the incubated cells and subjected to gelatin zymography as described under "Experimental Procedures". Arrowheads indicate the gelatinolytic bands of progelatinase A at 66 kDa (upper), the intermediate form at 59 kDa (center), and the mature form at 57 kDa (lower). An arrow at 90 kDa indicates a gelatinolytic band of progelatinase B. Ordinate, molecular size in kDa.
Figure 6B:

Effect of Modified TIMP-2 and TIMP-2 on the Cell-mediated Activation of Progelatinase A It has been hypothesized that a complex formed between MT-MMP and TIMP-2 acts as a receptor of progelatinase A and the formation of the ternary complex is essential for the cell-mediated activation of progelatinase A (Strogin, A. Y., Marmer, B. L., Grant, G. A., and Goldberg, G. I. (1993) J. Biol. Chem. 268, 14033–14039; Strongin, A. Y., Collier, I., Bannikov, G., Marmer, B. L., Grant G. A., and Goldberg, G. I. (1995) J. Biol. Chem. 270, 5331–5338: Kinoshita, T., Sato, H., Okada, A., Ohuchi, E., Imai, K., Okada, Y., and Seiki, M. (1998) J. Biol. Chem. 273, 16098–16103). Since the matrilysin-unbound fraction of carbamylated TIMP-2 loses the reactive site for interacting with the active site of MMPs while retaining the progelatinase A-binding site, the modified TIMP-2 may be able to prevent the formation of the ternary complex by competing for the limited number of the TIMP-2 binding site of progelatinase A. To examine this possibility, various concentrations of the modified and unmodified TIMP-2 forms and native TIMP-2 were added to the CM of concanavalin A-stimulated HT1080 cells and various species of endogenous gelatinase A in the cell lysates and those in the CM were analyzed by gelatin zymography. As shown in FIG. 6A, cell-associated mature form of gelatinase A was gradually diminished with increasing concentrations of the modified inactive. TIMP-2 in the matrilysin-unbound fraction. Progelatinase A and progelatinase B in the cell lysates were not affected by the modified TIMP-2. These detected zymogens may be proteins that have not been secreted from cells yet. In the CM, the intermediate form of gelatinase A did not remarkably diminish in the presence of the modified TIMP-2, whereas the mature form of gelatinase A almost disappeared as the concentration of the modified TIMP-2 was increased to 36 nM or higher. However, the amount of progelatinase A increased with increasing concentrations of the TIMP-2 (FIG. 6B). This suggests that the conversion of endogenous progelatinase A to the intermediate form was partially inhibited, whereas the conversion of the intermediate form to the mature one was strongly inhibited in the presence of high concentrations of the modified TIMP-2. The disappearance of the mature form of gelatinase A in the CM was in parallel with the diminution of the cell-associated mature form. Therefore, the conversion of the intermediate form to the mature one may depend on the cell-associated active gelatinase A. On the other hand, when varying concentrations of the active TIMP-2 in the matrilysin-bound fraction were added into the culture of HT1080 cells, the cell-associated mature form of gelatinase A increased slightly at 4.5 nM active TIMP-2, and then sharply diminished at higher concentrations (FIG. 6A). Both the mature and intermediate forms of gelatinase A in the CM disappeared, whereas progelatinase A increased with increasing concentrations of the active TIMP-2, suggesting that processing of progelatinase A by MT-MMP was inhibited in the presence of the active TIMP-2. The disappearance of the mature and intermediate forms of gelatinase A in the CM was also in parallel with the diminution of the cell-associated mature form. As the inhibition of the processing of progelatinase A by the active TIMP-2 did not increase the amount of cell-associated progelatinase A, the cell-associated zymogen may be released from the cell surface at high concentrations of the TIMP-2.

The effects of native TIMP-2 on the cell-associated gelatinase A and on the cell-mediated activation of progelatinase A were almost the same as those of the active TIMP-2 in the matrilysin-bound fraction (data not shown).

When the modified TIMP-2 was added to culture medium of concanavalin A-stimulated HT1080 cells in the foregoing examples, the conversion of endogenous progelatinase A to the intermediate form was partially inhibited, whereas that of the intermediated form to the mature one was strongly inhibited. The modified TIMP-2 of the present invention also prevented an accumulation of active gelatinase A on the cell surface. Without wishing to be bound to any theory, we speculate that occupation of the hemopexin-like domain of gelatinase A by the modified TIMP-2 makes it unable for gelatinase A to be retained on the cell surface, thus preventing the autocatalytic conversion of the intermediate form of gelatinase A to its mature form.

We also speculate that the conversion of the intermediate form of gelatinase A to the mature one depends upon the cell-associated activity of gelatinase A, and therefore, deprivation of the cell-associated active form of gelatinase A by the modified TIMP-2 causes an inhibition of production of the mature form. In the presence of high concentrations of the modified TIMP-2, the disappearance of the mature form of gelatinase A in the CM was indeed in parallel with the diminution of the cell-associated active gelatinase A (FIG. 6).

Considering the importance of formation of the ternary complex consisting of MT-MMP, TIMP-2 and (pro) gelatinase A, the inhibition of the cell-mediated activation of progelatinase A by TIMP-1 could be explained in two alternative ways. One explanation is that excess TIMP-2 occupies both the active site of MT-MMP and the TIMP-2-binding site in hemopexin-like domain of (pro)gelatinase A, thus preventing the formation of the ternary complex (FIG. 7B). The other explanation Is that TIMP-2 inhibits the catalytic activity of MT-MMP, thus inhibiting the proteolytic processing of progelatinase A.

We found that native TIMP-2, as well as modified TIMP-2, could prevent accumulation of active gelatinase A on the cell surface, without increasing the cell-associated progelatinase A. These data suggest that prevention of the formation of ternary complex contributes to the TIMP-2 inhibition of the cell-mediated activation of progelatinase A.

Excessive native TIMP-2, but not the modified TIMP-2, inhibited a production of the intermediate form of gelatinase A. Therefore, it is also likely that inhibition of the catalytic activity of MT-MMP by TIMP-2 contributes to inhibition of the processing of progelatinase A. As disappearance of the mature and the intermediate forms of gelatinase A in the CM and diminution of the cell-associated active gelatinase A were observed at the similar concentrations of unmodified TIMP-2 (FIG. 6), prevention of formation of the ternary complex and inhibition of MT-MMP activity may occur, simultaneously, at a critical concentration of TIMP-2 (FIG. 7B). It is likely that both mechanisms make TIMP-2 a potent regulator of the cell-mediated activation of progelatinase A.

We clarified the activation mechanism of MMPs by TIMPs to ensure that reactions promoted by the formation of a complex of a TIMP can be controlled or inhibited by a modified form of the TIMP. However, the enzymatic activity function of the MMP itself to which the NH$_2$ terminus binds is not affected For example, a modified TIMP-2 of the present invention can inhibit the activation of progelatinase. A without inhibiting the catalytic activity of MT1-MMP (FIG. 7A).

In studies of metastasis of cancer, a number of metalloenzyme inhibitors that directly inhibit MMP activity were investigated and examined. For example, they include BE-16627B, S1–27, etc. However, these MMP inhibitors were shown to have various side effects because they extensively inhibit MMP activity.

A possible means to inhibit the formation of a complex including a TIMP is to administer an excessive amount of the native form of the TIMP (FIG. 7B). However, this may rather promote the formation of the complex until the amount reaches a critical level. Moreover, the excessive TIMP may inhibit the MMP activity itself.

In contrast, modified TIMPs of the present invention can inhibit the activation of precursor MMPs specifically to the TIMP type without inhibiting the enzymatic activity of the MMPs itself as described above. Therefore, they have no problem of side effects or the like as described above and are also useful as test reagents.

What is claimed is:

1. A modified tissue inhibitor of metalloproteinase (TIMP) wherein the $NH_2$-terminal α-amino group thereof is modified with an electron-accepting group to lose the ability to bind to a metalloproteinase.

2. The modified TIMP of claim 1, which is a modified TIMP-2.

3. The modified TIMP of claim 1, wherein said electron-accepting group is a carbamyl group.

4. A pharmaceutical composition comprising the modified TIMP of claim 1, in combination with a pharmaceutically acceptable carrier.

5. The pharmaceutical composition of claim 4 used for the inhibition of metastasis of cancer or the inhibition of vascularization.

* * * * *

SEQUENCE LISTING

```
<160> NUMBER OF SEQ ID NOS:  5

<210> SEQ ID NO 1
<211> LENGTH: 207
<212> TYPE: PRT
<213> ORGANISM: Artificial Sequence
<220> FEATURE:
<223> OTHER INFORMATION: Description of Artificial Sequence: modified
      TIMP

<400> SEQUENCE: 1

Met Ala Pro Phe Glu Pro Leu Ala Ser Gly Ile Leu Leu Leu Tr
 1               5                  10                  15

Leu Ile Ala Pro Ser Arg Ala Cys Thr Cys Val Pro Pro His Pro Gl
            20                  25                  30

Thr Ala Phe Cys Asn Ser Asp Leu Val Ile Arg Ala Lys Phe Val Gl
        35                  40                  45

Thr Pro Glu Val Asn Gln Thr Thr Leu Tyr Gln Arg Tyr Glu Ile Ly
    50                  55                  60

Met Thr Lys Met Tyr Lys Gly Phe Gln Ala Leu Gly Asp Ala Ala As
65                  70                  75                  8

Ile Arg Phe Val Tyr Thr Pro Ala Met Glu Ser Val Cys Gly Tyr Ph
                85                  90                  95

His Arg Ser His Asn Arg Ser Glu Glu Phe Leu Ile Ala Gly Lys Le
            100                 105                 110

Gln Asp Gly Leu Leu His Ile Thr Thr Cys Ser Phe Val Ala Pro Tr
        115                 120                 125

Asn Ser Leu Ser Leu Ala Gln Arg Arg Gly Phe Thr Lys Thr Tyr Th
    130                 135                 140

Val Gly Cys Glu Glu Cys Thr Val Phe Pro Cys Leu Ser Ile Pro Cy
145                 150                 155                 16

Lys Leu Gln Ser Gly Thr His Cys Leu Trp Thr Asp Gln Leu Leu Gl
                165                 170                 175

Gly Ser Glu Lys Gly Phe Gln Ser Arg His Leu Ala Cys Leu Pro Ar
            180                 185                 190

Glu Pro Gly Leu Cys Thr Trp Gln Ser Leu Arg Ser Gln Ile Ala
        195                 200                 205

<210> SEQ ID NO 2
<211> LENGTH: 220
<212> TYPE: PRT
<213> ORGANISM: Artificial Sequence
<220> FEATURE:
<223> OTHER INFORMATION: Description of Artificial Sequence: modified
      TIMP

<400> SEQUENCE: 2
```

-continued

```
Met Gly Ala Ala Ala Arg Thr Leu Arg Leu Ala Leu Gly Leu Leu Leu
 1               5                  10                  15

Leu Ala Thr Leu Leu Arg Pro Ala Asp Ala Cys Ser Cys Ser Pro Val
             20                  25                  30

His Pro Gln Gln Ala Phe Cys Asn Ala Asp Val Val Ile Arg Ala Lys
         35                  40                  45

Ala Val Ser Glu Lys Glu Val Asp Ser Gly Asn Asp Ile Tyr Gly Asn
     50                  55                  60

Pro Ile Lys Arg Ile Gln Tyr Glu Ile Lys Gln Ile Lys Met Phe Lys
 65                  70                  75                  80

Gly Pro Glu Lys Asp Ile Glu Phe Ile Tyr Thr Ala Pro Ser Ser Ala
                 85                  90                  95

Val Cys Gly Val Ser Leu Asp Val Gly Gly Lys Lys Glu Tyr Leu Ile
             100                 105                 110

Ala Gly Lys Ala Glu Gly Asp Gly Lys Met His Ile Thr Leu Cys Asp
         115                 120                 125

Phe Ile Val Pro Trp Asp Thr Leu Ser Thr Gln Lys Lys Ser Leu
130                 135                 140

Asn His Arg Tyr Gln Met Gly Cys Glu Cys Lys Ile Thr Arg Cys Pro
145                 150                 155                 160

Met Ile Pro Cys Tyr Ile Ser Ser Pro Asp Glu Cys Leu Trp Met Asp
                 165                 170                 175

Trp Val Thr Glu Lys Asn Ile Asn Gly His Gln Ala Lys Phe Phe Ala
                 180                 185                 190

Cys Ile Lys Arg Ser Asp Gly Ser Cys Ala Trp Tyr Arg Gly Ala Ala
             195                 200                 205

Pro Pro Lys Gln Glu Phe Leu Asp Ile Glu Asp Pro
             210                 215                 220

<210> SEQ ID NO 3
<211> LENGTH: 211
<212> TYPE: PRT
<213> ORGANISM: Artificial Sequence
<220> FEATURE:
<223> OTHER INFORMATION: Description of Artificial Sequence: modified
      TIMP

<400> SEQUENCE: 3

Met Thr Pro Trp Leu Gly Leu Ile Val Leu Leu Gly Ser Trp Ser Leu
 1               5                  10                  15

Gly Asp Trp Gly Ala Glu Ala Cys Thr Cys Ser Pro Ser His Pro Gln
             20                  25                  30

Asp Ala Phe Cys Asn Ser Asp Ile Val Ile Arg Ala Lys Val Val Gly
         35                  40                  45

Lys Lys Leu Val Lys Glu Gly Pro Phe Gly Thr Leu Val Tyr Thr Ile
     50                  55                  60

Lys Gln Met Lys Met Tyr Arg Gly Phe Thr Lys Met Pro His Val Gln
 65                  70                  75                  80

Tyr Ile His Thr Glu Ala Ser Glu Ser Leu Cys Gly Leu Lys Leu Glu
                 85                  90                  95

Val Asn Lys Tyr Gln Tyr Leu Leu Thr Gly Arg Val Tyr Asp Gly Lys
             100                 105                 110

Met Tyr Thr Gly Leu Cys Asn Phe Val Glu Arg Trp Asp Gln Leu Thr
         115                 120                 125

Leu Ser Gln Arg Lys Gly Leu Asn Tyr Arg Tyr His Leu Gly Cys Asn
```

-continued

```
                130                 135                 140
Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Tyr Cys
                180                 185                 190

Ser Trp Tyr Arg Gly Trp Ala Pro Pro Asp Lys Ser Ile Ile Asn Ala
        195                 200                 205

Thr Asp Pro
    210

<210> SEQ ID NO 4
<211> LENGTH: 224
<212> TYPE: PRT
<213> ORGANISM: Artificial Sequence
<220> FEATURE:
<223> OTHER INFORMATION: Description of Artificial Sequence: modified
      TIMP

<400> SEQUENCE: 4

Met Pro Gly Ser Pro Arg Pro Ala Pro Ser Trp Val Leu Leu Leu Arg
  1               5                  10                  15

Leu Leu Ala Leu Leu Arg Pro Pro Gly Leu Gly Glu Ala Cys Ser Cys
                20                  25                  30

Ala Pro Ala His Pro Gln Gln His Ile Cys His Ser Ala Leu Val Ile
                35                  40                  45

Arg Ala Lys Ile Ser Ser Glu Lys Val Val Pro Ala Ser Ala Asp Pro
 50                  55                  60

Ala Asp Thr Glu Lys Met Leu Arg Tyr Glu Ile Lys Gln Ile Lys Met
 65                  70                  75                  80

Phe Lys Gly Phe Glu Lys Val Lys Asp Val Gln Tyr Ile Tyr Thr Pro
                    85                  90                  95

Phe Asp Ser Ser Leu Cys Gly Val Lys Leu Glu Ala Asn Ser Gln Lys
                100                 105                 110

Gln Tyr Leu Leu Thr Gly Gln Val Leu Ser Asp Gly Lys Val Phe Ile
                115                 120                 125

His Leu Cys Asn Tyr Ile Glu Pro Trp Glu Asp Leu Ser Leu Val Gln
                130                 135                 140

Arg Glu Ser Leu Asn His His Tyr His Leu Asn Cys Gly Cys Gln Ile
145                 150                 155                 160

Thr Thr Cys Tyr Thr Val Pro Cys Thr Ile Ser Ala Pro Asn Glu Cys
                165                 170                 175

Leu Trp Thr Asp Trp Leu Leu Glu Arg Lys Leu Tyr Gly Tyr Gln Ala
                180                 185                 190

Gln His Tyr Val Cys Met Lys His Val Asp Gly Thr Cys Ser Trp Tyr
                195                 200                 205

Arg Gly His Leu Pro Leu Arg Lys Glu Phe Val Asp Ile Val Gln Pro
                210                 215                 220

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: synthetic
      peptide
<221> NAME/KEY: MOD_RES
```

```
<222> LOCATION: (7)
<223> OTHER INFORMATION: modified Val
<221> NAME/KEY: MOD_RES
<222> LOCATION: (10)
<223> OTHER INFORMATION: modified Lys

<400> SEQUENCE: 5

Arg Pro Lys Pro Tyr Ala Xaa Trp Met Xaa Lys
 1               5                  10
```